United States Patent [19]
Yoshida et al.

[11] Patent Number: 5,324,852
[45] Date of Patent: Jun. 28, 1994

[54] 4-SUBSTITUTED-2-HYDROXYBUTANO-ATES AND A PROCESS FOR PRODUCING THEM

[75] Inventors: Naoyuki Yoshida; Kazutoshi Miyazawa, both of Ichihara, Japan

[73] Assignee: Chisso Corporation, Osaka, Japan

[21] Appl. No.: 974,825

[22] Filed: Nov. 16, 1992

Related U.S. Application Data

[62] Division of Ser. No. 730,989, Jul. 16, 1991, abandoned.

[30] Foreign Application Priority Data

Jul. 17, 1990 [JP] Japan ................................. 2-187095

[51] Int. Cl.$^5$ ..................... C07C 255/03; C07F 5/06
[52] U.S. Cl. .................... 558/347; 558/332; 558/352; 558/441; 560/184
[58] Field of Search ............. 558/332, 347, 352, 441; 560/184

[56] References Cited

U.S. PATENT DOCUMENTS

| 4,335,255 | 6/1982 | Krespan | 560/184 |
| 4,348,535 | 8/1982 | Schmidt | 560/184 |
| 4,495,190 | 1/1985 | Hagberg et al. | 514/262 |

FOREIGN PATENT DOCUMENTS

| 0233728 | 8/1987 | European Pat. Off. |
| 2132614 | 7/1984 | United Kingdom |

OTHER PUBLICATIONS

Chem. Abstracts, vol. 97, No. 3; 23301r (1982).
Chem. Abstracts, vol. 102, No. 23;204243r (1985).

Primary Examiner—Johann Richter
Attorney, Agent, or Firm—Wenderoth, Lind & Ponack

[57] ABSTRACT

The present invention provides an optically active 4-substituted-2-hydroxybutanoate represented by the general formula:

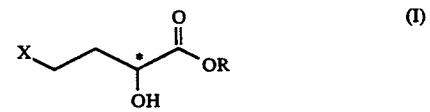

(I)

wherein X is Cl, Br, I or Cn, R is alkyl, and * shows an asymmetric carbon.

The compounds which are useful as starting materials for medical agents, are obtained by a process comprising ring-opening optically active α-hydroxy-γ-butyrolactone and esterifying the compound obtained.

6 Claims, No Drawings

4-SUBSTITUTED-2-HYDROXYBUTANOATES AND A PROCESS FOR PRODUCING THEM

This application is a division of now abandoned application Ser. No. 07/730,989, filed Jul. 16, 1991, now abandoned.

BACKGROUND OF THE INVENTION

1. Field of the Invention

The present invention relates to optically active 4-substituted-2-hydroxybutanoates which are useful as starting materials for medical agents and to a process for producing them.

2. Descriptions of the Prior Art

Optically active 4-substituted-2-hydroxybutanoates of the present invention are useful as starting materials of many medical agents. However, there has been no effective process so that racemic methyl 4-chloro-2-hydroxybutanoate, racemic methyl 4-bromo-2-hydroxybutanoate and the like were used (European Patent Laid-open Application No. 233728, etc.).

Recently, when racemic compounds are used as medical agents, it is necessary to examine the physiological activity of two enantiomorphs, because the physiologically activities may be different. Further, when a compound having a stereostructure has especially strong physiological activity, it is earnestly required to construct only a compound having the desired stereostructure, considering the efficiency and safety.

SUMMARY OF THE INVENTION

The inventors of the present invention have developed optically active 4-substituted-2-hydroxybutanoates which become useful compounds as starting materials of pharmaceuticals, and they found an effective process for producing the esters.

Namely, the present invention provides an optically active 4-substituted-2-hydroxybutanoate represented by the general formula:

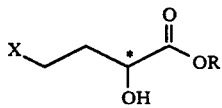

wherein X is Cl, Br, I or CN, R is alkyl of 1–10 carbon atoms, and * shows an asymmetric carbon.

Further, the present invention provides a process for producing said optically active 4-substituted-2-hydroxybutanoates represented by the general formula (I), which comprises ring-opening an optically active α-hydroxy-γ-butyrolactone as an intermediate compound of the formula:

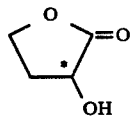

wherein * shows an asymmetric carbon, and esterifying the compound obtained.

The following description illustrates this invention more specifically.

Optically active 4-substituted-2-hydroxybutanoates of the present invention are represented by the above general formula (I). As these compounds, the following compounds are exemplified:

R-methyl 4-chloro-2-hydroxybutanoate,
R-ethyl 4-chloro-2-hydroxybutanoate,
R-propyl 4-chloro-2-hydroxybutanoate,
R-butyl 4-chloro-2-hydroxybutanoate,
R-pentyl 4-chloro-2-hydroxybutanoate,
S-methyl 4-chloro-2-hydroxybutanoate,
S-ethyl 4-chloro-2-hydroxybutanoate,
S-propyl 4-chloro-2-hydroxybutanoate,
S-butyl 4-chloro-2-hydroxybutanoate,
S-pentyl 4-chloro-2-hydroxybutanoate,
R-methyl 4-bromo-2-hydroxybutanoate,
R-ethyl 4-bromo-2-hydroxybutanoate,
R-propyl 4-bromo-2-hydroxybutanoate,
R-butyl 4-bromo-2-hydroxybutanoate,
R-pentyl 4-bromo-2-hydroxybutanoate,
S-methyl 4-bromo-2-hydroxybutanoate,
S-ethyl 4-bromo-2-hydroxybutanoate,
S-propyl 4-bromo-2-hydroxybutanoate,
S-butyl 4-bromo-2-hydroxybutanoate,
S-pentyl 4-bromo-2-hydroxybutanoate,
R-methyl 4-iodo-2-hydroxybutanoate,
R-ethyl 4-iodo-2-hydroxybutanoate,
R-propyl 4-iodo-2-hydroxybutanoate,
R-butyl 4-iodo-2-hydroxybutanoate,
R-pentyl 4-iodo-2-hydroxybutanoate,
S-methyl 4-iodo-2-hydroxybutanoate,
S-ethyl 4-iodo-2-hydroxybutanoate,
S-propyl 4-iodo-2-hydroxybutanoate,
S-butyl 4-iodo-2-hydroxybutanoate,
S-pentyl 4-iodo-2-hydroxybutanoate,
R-methyl 4-cyano-2-hydroxybutanoate,
R-ethyl 4-cyano-2-hydroxybutanoate,
R-propyl 4-cyano-2-hydroxybutanoate,
R-butyl 4-cyano-2-hydroxybutanoate,
R-pentyl 4-cyano-2-hydroxybutanoate,
S-methyl 4-cyano-2-hydroxybutanoate,
S-ethyl 4-cyano-2-hydroxybutanoate,
S-propyl 4-cyano-2-hydroxybutanoate,
S-butyl 4-cyano-2-hydroxybutanoate,
S-pentyl 4-cyano-2-hydroxybutanoate and the like.

The optically active 4-substituted-2-hydroxybutanoates of the present invention are obtained by ring-opening an optically active α-hydroxy-γ-butyrolactone represented by the above formula (II) which is obtained by optical resolution wherein racemic α-hydroxy-γbutyrolactone is transesterified with ethyl acetate, a fatty acid vinyl ester, a triglyceride or the like in the presence of an esterase produced by a microorganism or an esterase from an animal as a catalyst, and esterifying the compound obtained.

The racemic α-hydroxy-γ-butyrolactone as a raw material can be easily obtained from α-bromo-γ-butyrolactone by a method of Goal et al. (Organic Preparations and Procedures Int., 17, 91 (1985)).

As fatty acid vinyl esters used int he transesterification reaction, vinyl acetagte, vinyl propionate, vinyl butyrate, vinyl caproate, vinyl laurate, etc. can be used. As triglycerides, triacetin, tripropionin, tributyrin, tricaproin, trilaurin etc. can be exemplified. These compounds are commercially available without any difficulty.

The following table shows commercially available esterases.

TABLE

| Trade name | Origin | Seller or Maker |
| --- | --- | --- |
| Lipase PS | Pseudomonas fluorescens | Amono Pharmaceutical Co., Ltd |
| Li-pase CES | Pseudomonas sp | Amono Pharmaceutical Co., Ltd |
| Lipase AP | Aspergillus niger | Amono Pharmaceutical Co., Ltd |
| Lipase M | Mucor javanicus | Amono Pharmaceutical Co., Ltd |
| Lipase CE | Humicola lanuginosa | Amono Pharmaceutical Co., Ltd |
| Lipase F-AP | Rhizopus javanicus | Amono Pharmaceutical Co., Ltd |
| Lipase II | Porcine Pancreas | Sigma Chemical Co., Ltd |
| Lipase VIII | Geotrichum Candidum | Sigma Chemical Co., Ltd |
| Lipase X | Rhizopus delamar | Sigma Chemical Co., Ltd |
| Lipase | Chromobacterium Viscosum | Toyo Jozo Co., Ltd |
| Lipase A | Aspergillus niger | Novo Industi A/S |
| Lipase | Rhizopus niveus | Nagase Biochemicals, Ltd. |
| Lipase B | Pseudomonas fragi | Sapporo Beer Co. |

In addition to these esterases, the enzymes produced from microorganisms can be used. These microorganisms which produce the enzymes having the above reaction ability can be used regardless of their species and genus. As such microorganisms, the genera Pseudomonas, Arthrobacter, Acromobacter, Alcaligenes, Aspergillus, Chroaobacterium, Candida, Mucor, Rhizopus, etc. can be exemplified.

In these microorganisms, particularly the genus Pseudomonas is preferred.

The transesterification reaction is conducted by mixing a racemic α-hydroxy-γ-butyrolactone with ethyl acetate, a fatty acid vinyl ester or a triglyceride and efficiently contacting the mixture with an esterase. The reaction temperature is suitably from room temperature (about 10° C.) to 150° C., especially and preferably from 20° to 45° C. The reaction time is from 1 to 1000 hours. α-hydroxy-γ-butyrolactone and ethyl acetate, the fatty acid vinyl ester or the triglyceride are suitably mixed in the ratio from 1:0.5 to 1:10 by mole, preferably 10.5 by mole.

When necessary, n-hexane, n-heptane, benzene, toluene, ethyl ether, etc. can be used as a solvent by which esterase activity is not inhibited. The solvent may be omitted.

After the transesterification reaction is conducted, the esterase can be removed by conventional filter operation and used again, as it is. After concentrating the filtrate, optically active α-hydroxy-γ-butyrolactone and an optically active α-acyloxy-γ-butyrolactone can be separated by vacuum distillation or column chromatography, respectively. When these lactones have insufficient optical purities, each lactone is re-transesterified (in the case of the acyl compound, after the acyl group is hydrolyzed) to obtain a high optically pure compound.

The optically active α-hydroxy-γ-butyrolactone obtained can lead to the production of optically active 4-chloro-2-hydroxybutanoate or optically active 4-bromo-2-hydroxybutanoate by reaction with ethyl alcohol saturated with hydrogen chloride or hydrogen bromide.

Further, optically active α-hydroxy-γ-butyrolactone can lead to the production of optically active 4-iodo-2-hydroxybutanoate by reaction with trimethylsilyl chloride and sodium iodide or trimethylsilyl iodide.

Moreover, optically active α-hydroxy-γ-butyrolactone can lead to the production of optically active 4-cyano-2-hydroxybutanoate by reaction with trimethylsilylcyanide. Otherwise, it can lead to the production of optically active 4-cyano-2-hydroxybutanoate by cyanizing optically active 4-halo-2-hydroxybutanoate.

By using the above operation, the R- and S-compounds of optically active 4-substituted-2-hydroxybutanoate can be obtained, respectively.

Optically active 4-substituted-2-hydroxybutanoates of the present invention are useful and applicable compounds as starting materials of medical agents. For example, optically active guanine derivatives (U.S. Pat. No. 4,495,190 etc.) which are useful as physiologically active materials can be obtained. Otherwise, as to calcium channel blockers (Japanese Patent Laid-open Application No. 61-87503, etc.), optically active materials by which more effective activity is expected can be obtained.

DESCRIPTION OF THE PREFERRED EMBODIMENTS

The following examples illustrate the present invention more specifically, but these will not always be precise in practical applications.

Example 1

(i) Production of R-(+)-α-hydroxy-q-butyrolactone

A mixture of 15.3 g of racemic-α-hydroxy-γ-butyrolactone, 6.5 g of vinyl acetate and 5 g of lipase PS (manufactured by Amano Pharmaceutical Co., Ltd.) was put into a 100 ml flask. The mixture was stirred for 6 hours at room temperature. After lipase PS was removed by filtration, the filtrate was concentrated and about 40 g of liquid was obtained. The liquid was column-chromatographed (toluene/ethyl acetate (10/1)), and 5.2 g of S-(−)-α-hydroxy-γ-butyrolactone ($[\alpha]_D$−57.6° (c 1.22, $CHCl_3$), 99% ee) and 7.2 g of R-(+)-α-acetyloxy-γ-butyrolactone ($[\alpha]_D$+32.6° (c 0.87, $CHCl_3$), 70% ee) were separated, respectively.

R-(+)-α-acetyloxy-γ-butyrolactone was dissolved into a mixed solvent of 50 ml of 1,4-dioxane and 30 ml of ethanol, and 3.8 g of potassium carbonate was added. The mixture was stirred for 5 hours at room temperature. After the mixture was neutralized with hydrochloric acid, the salt separated was removed by filtration. Moreover, after removing ethanol, the filtrate was purified by distillation, and 6.1 g of R-(+)-α-hydroxy-γ-butyrolactone was obtained.

(ii) Production of R-ethyl (+)-4-chloro-2-hydroxybutanoate 1.6 g of R-(+)-α-hydroxy-65 -butyrolactone (90% ee) was dissolved into 200 ml of ethanol, and the solution was put into a 300 ml three-necked flask. Hydrogen chloride gas was blown into the three-necked flask, and the solution was stirred in a saturated condition at room temperature overnight. After hydrogen chloride gas was removed thoroughly by blowing nitrogen through the solution, ethanol was distilled away, and the residue was extracted with ether. The ether layer was washed with sodium bicarbonate and then with a saturated saline solution. After the ether layer was dried on anhydrous magnesium sulfate, ether was distilled away. The residue was distilled under reduced pressure to obtain 2.1 g of the desired R-ethyl (+)-4-chloro-2-hydroxybutanoate. The physical properties of the compound are as follows.

Boiling point: 112° C./17 mmHg
Specific rotation: $[\alpha]_D+6.1°$ (C1.9, CHCl$_3$)

Example 2

Production of S-ethyl (-)-4-chloro-hydroxybutanoate 1.6 g of S-(−)-α-hydroxy-γ-butyrolactone (90% ee) was dissolved into 200 ml of ethanol, and the solution was put into a 300 ml three-necked flask. Hydrogen chloride gas was blown into the three-necked flask, and the solution was stirred in a saturated condition at room temperature overnight. After hydrogen chloride gas was removed thoroughly by blowing nitrogen through the solution, ethanol was distilled away, and the residue was extracted with ether. The ether layer was washed with sodium bicarbonate and then with a saturated saline solution. After the ether layer was dried on anhydrous magnesium sulfate, ether was distilled away. The residue was distilled under reduced pressure to obtain 2.0 g of the desired S-ethyl (−)-4-chloro-2-hydroxy butanoate. The physical properties of the compound are as follows.

Boiling point: 101° C./13 mmHg
Specific rotation: $[\alpha]_D-6.7°$ (C1.2, CHCl$_3$)

Example 3

Production of R-ethyl (+)-4-iodo-2-hydroxybutanoate 20 ml of an acetonitrile solution of trimethylsilyl chloride was slowly added into 50 ml of an acetonitrile solution containing 1.3 g of R-(+)-α-hydroxy-γ-butyrolactone (70% ee) and 5.7 g of sodium iodide. After the solution was heated under reflux for 14 hours, 10 ml of ethanol was added dropwise and the solution was stirred at room temperature for 10 minutes.

Acetonitrile was distilled away, and ether was added to the residue. The ether layer was washed with sodium bicarbonate and then with a saturated saline solution. After the ether layer was dried on anhydrous magnesium sulfate, ether was distilled away. 0.73 g of the desired R-ethyl (+)-4-iodo-2-hydroxybutanoate was obtained. Specific rotation: $[\alpha]_D+4.0°$ (C1.15, CHCl$_3$)

We claim:

1. A process for producing an optically active 4-substituted-2-hydroxybutanoate represented by the formula (I)

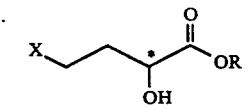

wherein X is Cl or Br, R is alkyl or 1-10 carbon atoms, and * shows an asymmetric carbon which comprises contacting a compound of the formula:

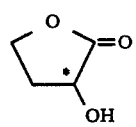

wherein * shows an asymmetric carbon with alkyl alcohol of 1-10 carbon atoms saturated with hydrogen chloride or hydrogen bromide to perform the following reactions (1) ring-opening of the compound of the formula (II), (2) introducing a Cl ion or a Br ion derived from said hydrogen chloride or hydrogen bromide into the fourth position of thus obtained ring-opened intermediate of the compound of the formula (II) and (3) introducing an alkyl group derived from said alkyl alcohol into the carbonyloxy portion of thus obtained ring-opened intermediate of the compound of the formula (II) in one step.

2. A process according to claim 1, wherein the alkyl alcohol is ethanol.

3. A process for producing an optically active 4-substituted-2-hydroxybutanoate represented by the formula (I)

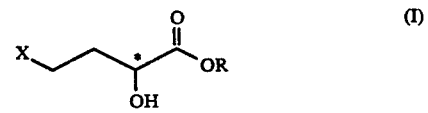

wherein X is I or CN, R is alkyl of 1-10 carbon atoms, and * shows an asymmetric carbon which comprises contacting a compound of the formula:

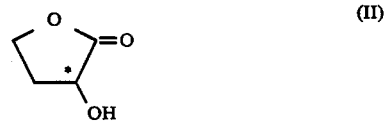

wherein * shows an asymmetric carbon with alkyl alcohol of 1-10 carbon atoms containing trimethylsilyl iodide or trimethylsilyl cyanide to perform the following reactions (1) ring-opening of the compound of the formula (II), (2) introducing a I ion or CN ion derived form said trimethylsilyl compound into the fourth position of thus obtained ring-opened intermediate of the compound of the formula (II) and (3) introducing an alkyl grouped derived from said alkyl alcohol into the caronyloxy portion of thus obtained ring-opened intermediate of the compound of the formula (II) in one step.

4. A process for producing an optically active 4-substituted-2-hydroxybutanoate represented by the formula (I)

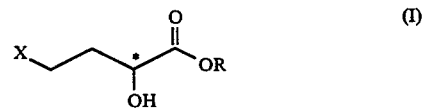

wherein X is I, R is alkyl of 1-10 carbon atoms, and * shows an asymmetric carbon which comprises contacting a compound of the formula

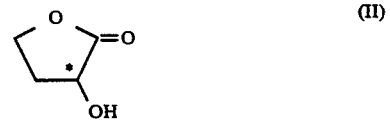

wherein * shows as asymmetric carbon with trimethylsilyl chloride and sodium iodide in a solvent to perform the following reactions (1) ring-opening of the compound of the formula (II) and (2) introducing a I ion derived from said sodium iodide into the fourth position of thus obtained ring-opened intermediate of the compound of the formula (II), and contacting the thus obtained I ion-introduced ring-opened intermediate with alkyl alcohol of 1-10 carbon atoms to introduce an alkyl group derived from said alkyl radical into the carbonyloxy portion of said I ion-introduced ring-opened intermediate.

5. A process according to claim 4, wherein the alkyl alcohol is ethanol.

6. A process according to claim 4, wherein the contacting of the compound (II) with trimethylsilyl chloride and sodium iodide is carried out in a solvent of acetonitrile.

* * * * *

UNITED STATES PATENT AND TRADEMARK OFFICE
CERTIFICATE OF CORRECTION

PATENT NO. : 5,324,852
DATED : June 28, 1994
INVENTOR(S) : NAOYUKI YOSHIDA and KAZUTOSHI MIYAZAWA It is certified that error appears in the above-indentified patent and that said Letters Patent is hereby corrected as shown below:

On the title page, in the ABSTRACT, line 5 (counting the formula as one line), change the term "Cn" to —CN—.

Column 1, lines 25 and 26, change "physiologically" to —physiological—.

Column 2, line 50, change "γbutyrolactone" to —γ-butyrolactone—;
line 60, change "int he" to —in the—;
line 61, change "acetagte" to —acetate—.

Column 3, in the TABLE, line 17, change "*delamar*" to —*delemar*—;
line 30, correct the spelling of "*Chromobacterium*";
line 44, change "10.5" to —1:0.5—.

Column 4, line 30, change "q" to —γ—;
line 55, change "65" to —γ—.

UNITED STATES PATENT AND TRADEMARK OFFICE
CERTIFICATE OF CORRECTION

PATENT NO. : 5,324,852
DATED : June 28, 1994
INVENTOR(S) : NAOYUKI YOSHIDA AND KAZUTOSHI MIYAZAWA It is certified that error appears in the above-indentified patent and that said Letters Patent is hereby corrected as shown below:

Column 5, line 7, after "chloro-" insert —2- —.

Column 6, line 37, change "grouped" to —group—;
       line 38, change "caronyloxy" to —carbonyloxy—.

Signed and Sealed this

Seventeenth Day of January, 1995

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,324,852
DATED : May 24, 1994
INVENTOR(S) : Fred Klatte

It is certified that error appears in the above-indentified patent and that said Letters Patent is hereby corrected as shown below:

In col. 2, line 50, change "Fe2SO4" to --$FeSO_4$--;
In col. 2, line 51, change "FeCl3" to --$FeCl_2$--;
In col. 5, line 43, change "Fe2SO4" to --$FeSO_4$--;
In col. 5, line 43, change "FeCl3" to --$FeCl_2$--;
In col. 8, line 36, change "Fe2SO4" to --$FeSO_4$--;
In col. 8, line 59, change "FeCl3" to --$FeCl_2$--;

In the Abstract:

In line 14, change "Fe2SO4" to --$FeSO_4$-- and "FeCl3" to --$FeCl_2$--.

Signed and Sealed this

Sixteenth Day of July, 1996

Attest:

BRUCE LEHMAN

*Attesting Officer*      *Commissioner of Patents and Trademarks*